United States Patent
Meeks et al.

(10) Patent No.: US 9,921,169 B2
(45) Date of Patent: Mar. 20, 2018

(54) METHOD OF DETECTING DEFECT LOCATION USING MULTI-SURFACE SPECULAR REFLECTION

(71) Applicant: Zeta Instruments, Inc., San Jose, CA (US)

(72) Inventors: Steven W. Meeks, Palo Alto, CA (US); Rusmin Kudinar, Fremont, CA (US); Ronny Soetarman, Fremont, CA (US); Hung P. Nguyen, Santa Clara, CA (US)

(73) Assignee: ZETA INSTRUMENTS, INC., San Jose, CA (US)

( * ) Notice: Subject to any disclaimer, the term of this patent is extended or adjusted under 35 U.S.C. 154(b) by 0 days.

(21) Appl. No.: 15/159,266

(22) Filed: May 19, 2016

(65) Prior Publication Data

US 2017/0336330 A1    Nov. 23, 2017

(51) Int. Cl.
  *G01N 21/55* (2014.01)
  *G01N 21/958* (2006.01)
  *G01N 21/94* (2006.01)

(52) U.S. Cl.
  CPC ........... *G01N 21/958* (2013.01); *G01N 21/55* (2013.01); *G01N 21/94* (2013.01); *G01N 2201/0683* (2013.01); *G01N 2201/06113* (2013.01); *G01N 2201/105* (2013.01)

(58) Field of Classification Search
  CPC ......... G01N 21/958; G01N 2021/8967; G01N 21/01; G01N 21/55; G01N 21/896; G01N 21/94; G01N 21/9501; G01N 21/9505; G01N 21/956; G01N 2021/4757; G01N 2021/4759; G01N 2021/4761; G01N 2021/8466
  See application file for complete search history.

(56) References Cited

U.S. PATENT DOCUMENTS

| | | | |
|---|---|---|---|
| 8,830,457 B1* | 9/2014 | Meeks | G01N 21/958 356/237.4 |
| 8,836,935 B1* | 9/2014 | Meeks | G01N 21/958 356/239.7 |
| 2014/0218724 A1* | 8/2014 | Meeks | G01N 21/9501 356/237.4 |

* cited by examiner

*Primary Examiner* — Michael P Stafira
(74) *Attorney, Agent, or Firm* — Imperium Patent Works; Mark D. Marrello

(57) ABSTRACT

A method for detecting defects includes directing a scanning beam to a location on a surface of a transparent sample, measuring top and bottom surface specular reflection intensity, and storing coordinate values of the first location and the top and bottom surface specular reflection intensity in a memory. The method may further include comparing the top surface specular reflection intensity measured at each location with a first threshold value, comparing the bottom surface specular reflection intensity measured at each location with a second threshold value, and determining if a defect is present at each location and on which surface the defect is present. The method may further include comparing the top surface specular reflection intensity measured at each location with a first intensity range, comparing the bottom surface specular reflection intensity measured at each location with a second intensity range, and determining on which surface the defect is present.

16 Claims, 14 Drawing Sheets

TRANSPARENCY MAY BE IN THE VISIBLE SPECTRUM OR THE INFRARED SPECTRUM.
GLASS IS TRANSPARENT IN THE VISIBLE AND SILICON IS TRANSPARENT IN THE INFRARED.

**TRANSPARENT SAMPLE
(CROSS-SECTIONAL VIEW)**

SPECULAR REFLECTION
(CROSS-SECTIONAL VIEW)

TOP AND BOTTOM SPECULAR REFLECTION MAPPING

SCATTERED RADIATION
DUE TO TOP SURFACE PARTICLE
(CROSS-SECTIONAL VIEW)

PRESENCE OF A DECREASE IN TOP SURFACE SPECULAR RADIATION MAP
INDICATES THAT A TOP PARTICLE IS PRESENT AT THE SCANNING LOCATION.

TOP AND BOTTOM SURFACE SPECULAR
REFLECTION MAPPING

SCATTERED RADIATION
DUE TO BOTTOM SURFACE PARTICLE
(CROSS-SECTIONAL VIEW)

PRESENCE OF ONLY A DECREASE IN BOTTOM SURFACE SPECULAR REFLECTION
INDICATES THAT A BOTTOM PARTICLE IS PRESENT AT THE SCANNING LOCATION.

BOTTOM SURFACE SPECULAR REFLECTION MAPPING

SPECULAR REFLECTION
(CROSS-SECTIONAL VIEW)

POLARIZED BOTTOM SPECULAR REFLECTION MAPPING

SCATTERED RADIATION
DUE TO TOP SURFACE PIT
(CROSS-SECTIONAL VIEW)

TOP AND BOTTOM SURFACE SPECULAR REFLECTION MAPPING

SCATTERED RADIATION
DUE TO BOTTOM SURFACE PIT
(CROSS-SECTIONAL VIEW)

BOTTOM SURFACE SPECULAR REFLECTION MAPPING

EXEMPLARY SEPARATION MIRROR SHAPES
SQUARE SHAPE 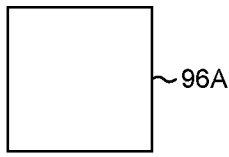 ~96A
CIRCULAR SHAPE 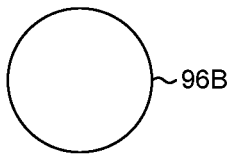 ~96B
OVAL SHAPE 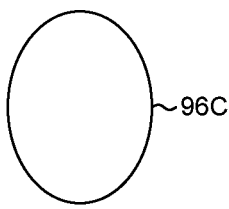 ~96C
D-SHAPED 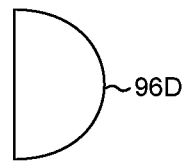 ~96D
SEPARATION ("PICK OFF") MIRROR SHAPES
FIG. 16

| DECREASE IN TOP SPECULAR REFLECTION? | DECREASE IN BOTTOM SPECULAR REFLECTION? | DEFECT LOCATION |
|---|---|---|
| YES | NO | TOP SURFACE |
| YES | YES | TOP SURFACE |
| NO | YES | BOTTOM SURFACE |

DEFECT DETECTION LOGIC TABLE

FIG. 17

| SIGNIFICANT CHANGE IN TOP SPECULAR REFLECTION? | SIGNIFICANT CHANGE IN BOTTOM SPECULAR REFLECTION? | DEFECT LOCATION |
|---|---|---|
| YES | NO | TOP SURFACE |
| YES | YES | TOP SURFACE |
| NO | YES | BOTTOM SURFACE |

DEFECT DETECTION LOGIC TABLE

FIG. 18

WORK PIECE DEFECT MAPPING

SEPARATION ("PICK OFF") MIRROR POSITION

METHOD OF DETECTING DEFECT LOCATION USING MULTI-SURFACE SPECULAR REFLECTION

TECHNICAL FIELD

The described embodiments relate generally to detecting defects and more particularly to detecting the location of a defect on a surface of a transparent sample.

BACKGROUND INFORMATION

Transparent solids are used to form various products such as display and touch screen devices. The inspection of transparent solids is complicated by the difficulty of separating specular reflection from the top surface of a transparent sample from specular reflection from the bottom surface of a transparent sample. This difficulty is further complicated when there is only time for a single scan to be performed at any given location on the transparent sample.

SUMMARY

In a first novel aspect, an optical inspector, including a time varying beam reflector, a radiating source that irradiates the time varying beam reflector, a telecentric scan lens configured to direct the radiation reflected by the time varying beam reflector onto a first surface of a transparent sample, where a portion of the radiation irradiates a second surface of the transparent sample. The optical inspector also includes a first detector that receives at least a portion of top surface specular reflection, where the top surface specular reflection results from the irradiation of the first surface of the transparent sample. The optical inspector also includes a second detector that receives at least a portion of the bottom surface specular reflection, where the bottom surface specular reflection results from the irradiation of the second surface of the transparent sample.

In a second novel aspect, an optical inspector, that includes a time varying beam reflector, a radiating source that irradiates the time varying beam reflector, a telecentric scan lens configured to direct the radiation reflected by the time varying beam reflector onto a first surface of a transparent sample, where a portion of the radiation irradiates a second surface of the transparent sample. The optical inspector also includes a first means for separating top surface specular reflection from bottom surface specular reflection, where the top surface specular reflection results from the irradiation of the first surface of the transparent sample, and where the bottom surface specular reflection results from the irradiation of the second surface of the transparent sample. The optical inspector further includes a second means for determining on which surface a defect is present.

In one example, an optical inspector includes a turning mirror, where the turning mirror is a switchable mirror that can be (i) adjusted to a first position where the turning mirror reflects the top surface specular reflection and the bottom surface specular reflection, and (ii) can be adjusted to a second position where the turning mirror does not reflect the top surface specular reflection or the bottom surface specular reflection.

In another example, the optical inspector includes a first polarizing element that receives the top surface specular reflection, where the first detector receives at least a portion of polarized top surface specular reflection that passed through the first polarizing element.

In yet another example, the optical inspector includes a second polarizing element that receives the bottom surface specular reflection, where the second detector receives at least a portion of polarized bottom surface specular reflection that passed through the second polarizing element.

In a third novel aspect, an optical inspector, includes a time varying beam reflector, a radiating source that irradiates the time varying beam reflector, a telecentric scan lens configured to direct the radiation reflected by the time varying beam reflector onto a first surface of a transparent sample, where a portion of the radiation irradiates a second surface of the transparent sample. The optical inspector also includes a first means for separating top surface specular reflection from bottom surface specular reflection, where the top surface specular reflection results from the irradiation of the first surface of the transparent sample, and where the bottom surface specular reflection results from the irradiation of the second surface of the transparent sample. The optical inspector also includes a second means for determining on which surface a defect is present.

In one example, the first means includes a separation mirror that is configured to only reflect specular reflection from one surface of the transparent sample.

In another example, the second means includes a first detector, and a second detector, wherein the first detector measures top surface specular reflection intensity, and wherein the second detector measures bottom surface specular reflection intensity.

In a fourth novel aspect, a method for detecting defects includes (a) directing a scanning beam to a first location on a first surface of a transparent sample, where a portion of the scanning beam irradiates a second surface of the transparent sample, (b) at the first location, measuring top surface specular reflection intensity and bottom surface specular reflection intensity, where the top surface specular reflection intensity results from irradiation by the scanning beam at the first location on the first surface of the transparent sample, and where the bottom surface specular reflection intensity results from irradiation by the scanning beam on the second surface of the transparent sample, and (c) storing coordinate values of the first location, the measured top surface specular reflection intensity, and the measured bottom surface specular reflection intensity in a memory.

In a fifth novel aspect, a method for detecting defects includes (a) directing a scanning beam to a first location on a first surface of a transparent sample, where a portion of the scanning beam irradiates a second surface of the transparent sample, (b) at the first location, measuring top surface specular reflection intensity and bottom surface specular reflection intensity, where both the top surface specular reflection intensity and the bottom surface specular reflection intensity result from irradiation by the scanning beam at the first location on the first surface of the transparent sample, and where the bottom surface specular reflection passes through a first polarizing element before the measurement of the bottom surface specular reflection intensity, and (c) storing coordinate values of the first location, the measured top surface specular reflection intensity, and the measured bottom surface specular reflection intensity in a memory.

In a first example, an optical inspector includes a turning mirror that is a switchable mirror that can be (i) adjusted to a first position where the turning mirror reflects the top surface specular reflection and the bottom surface specular reflection, and (ii) can be adjusted to a second position where the turning mirror does not reflect the top surface specular reflection or the bottom surface specular reflection.

In a second example, an optical inspector includes a first polarizing element that receives the top surface specular reflection, where the first detector receives at least a portion of polarized top surface specular reflection that passed through the first polarizing element.

In a third example, an optical inspector includes a second polarizing element that receives the bottom surface specular reflection, where the second detector receives at least a portion of polarized bottom surface specular reflection that passed through the second polarizing element.

Further details and embodiments and techniques are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 16 is a diagram illustrating exemplary separation mirror shapes.

FIG. 17 is a logic table illustrating a first method of detecting a defect location.

FIG. 18 is a logic table illustrating a second method of detecting a defect location.

DETAILED DESCRIPTION

Reference will now be made in detail to background examples and some embodiments of the invention, examples of which are illustrated in the accompanying drawings. In the description and claims below, relational terms such as "top", "down", "upper", "lower", "top", "bottom", "left" and "right" may be used to describe relative orientations between different parts of a structure being described, and it is to be understood that the overall structure being described can actually be oriented in any way in three-dimensional space.

Figure 1:
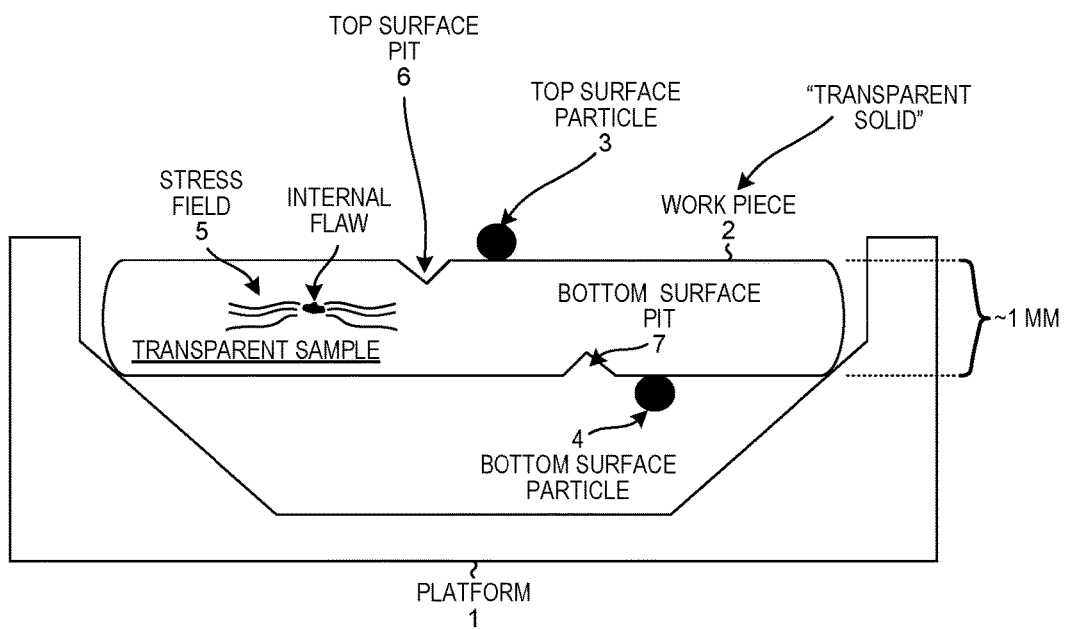
FIG. 1 is a cross-sectional diagram illustrating a transparent sample (also referred to as a "transparent solid" or a "work piece") supported by a platform.

FIG. 1 is a cross-sectional diagram illustrating a transparent sample supported by a platform. During the fabrication of transparent samples (also referred to transparent work pieces, transparent layers, transparent wafers, transparent solids and transparent discs) unwanted defects can be produced. These unwanted defects include a top surface particle 3, a bottom surface particle 4, a stress field 5, an internal flaw, a top surface pit 6, a bottom surface pit 7, top and bottom surface cracks (not shown), top and bottom surface stains (not shown), top and bottom surface scratches (not shown). These defects may occur in various locations on the transparent sample. These defects result in undesirable results such as reduced operating life of a resulting display device, non-functionality of the resulting display device, and degraded performance (light efficiency) of the resulting display device. It is valuable for a display manufacturer to detect these defects before additional resources are spent developing a product that will not function properly due to wafer level defects. For example, a top surface particle may produce unwanted shielding on the top surface of the transparent sample and may interfere with the ability to focus a lithography pattern on the surface. Particles on the top surface may also cause electrical shorts to appear when metal lines are deposited on this surface.

It is noted herein, the example of glass is used for exemplary use only. This disclosure is not limited to the detection of defects on glass. Rather, this disclosure is applicable to all transparent samples or wafers or discs regardless of the specific material constituting the sample/wafer/disc or the end device to be manufactured with the developed sample/wafer/disc. For example, silicon is opaque in the visible range of the spectrum but transparent in the infrared spectrum. Transparent samples may include at least the following materials: glass, plastic, quartz, sapphire, silicon, Silicon Carbide (SiC), and Gallium Nitride (GaN).

The transparent sample in FIG. 1 is approximately one millimeter thick. No other materials directly abut the top surface or bottom surface of the transparent sample. Rather, the top surface and bottom surface of the transparent sample abuts open air. Another typical means of supporting the transparent sample is to use a set of pins that support the bottom of the sample at regular intervals. It is noted herein, that other types of platforms exist and may be used to support a transparent sample. For example, a flat surface upon which the transparent sample rests may be used as a platform. In this example, the flat surface would contact the entire bottom surface of the transparent sample (therefore the bottom surface of the sample would not abut open air, but rather the transporting surface directly).

The transparent sample (work piece 2) in FIG. 1 has multiple defects: a top surface particle 3, a bottom surface particle 4, a stress field 5 caused by an internal flaw, a top surface pit 6, and a bottom surface pit 7.

Figure 2:
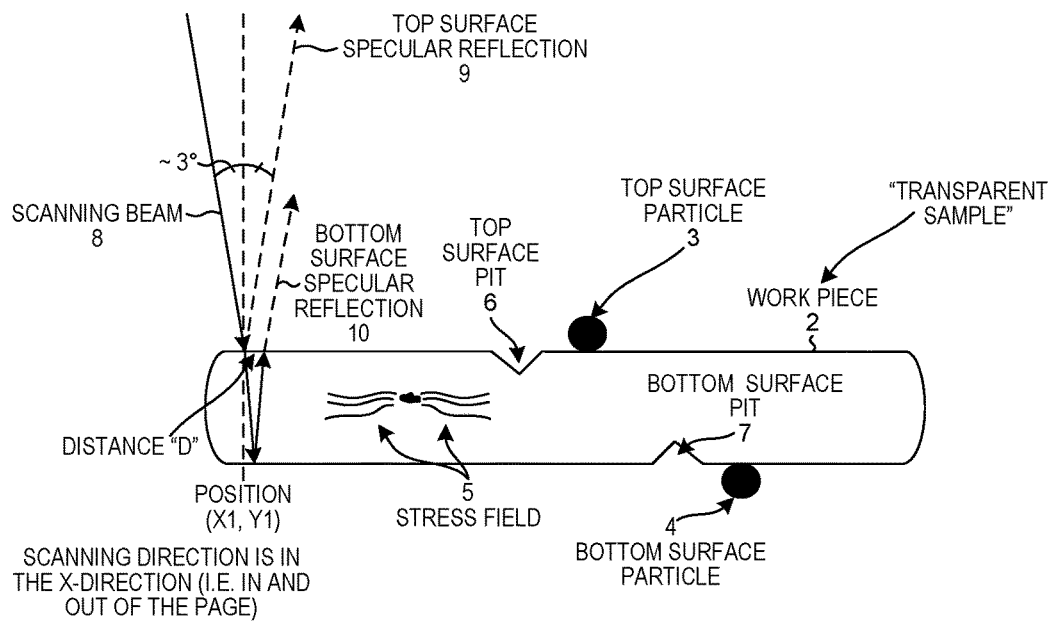
FIG. 2 is a cross-sectional diagram illustrating a scanning beam directed at position located at (X1, Y1) on the transparent sample.

FIG. 2 is a cross-sectional diagram illustrating the work piece 2 irradiated with a scanning beam 8 directed at position located at (X1, Y1). The scanning beam 8 scans across the work piece 2 in either the X-direction (in and out of the page) or the Y-direction. Significant top surface specular reflection 9 is reflected from the top surface of the work piece 2 (referred to as "top surface specular reflection"). Significant specular reflection 10 is also reflected from the bottom surface of the work piece 2 (referred to as "bottom surface specular reflection"). Top surface and bottom surface specular reflections 9 and 10 are of similar intensity when no defects are present on either surface of the work piece.

The top surface specular reflection 9 is emitted from the top surface of the work piece 2 at a similar angle to the scanning beam angle of incidence upon the top surface of the work piece 2. In the example shown in FIG. 2, the angle of incidence is three degrees from normal and the angle of specular reflection is three degrees from normal in the opposite direction.

Figure 14:
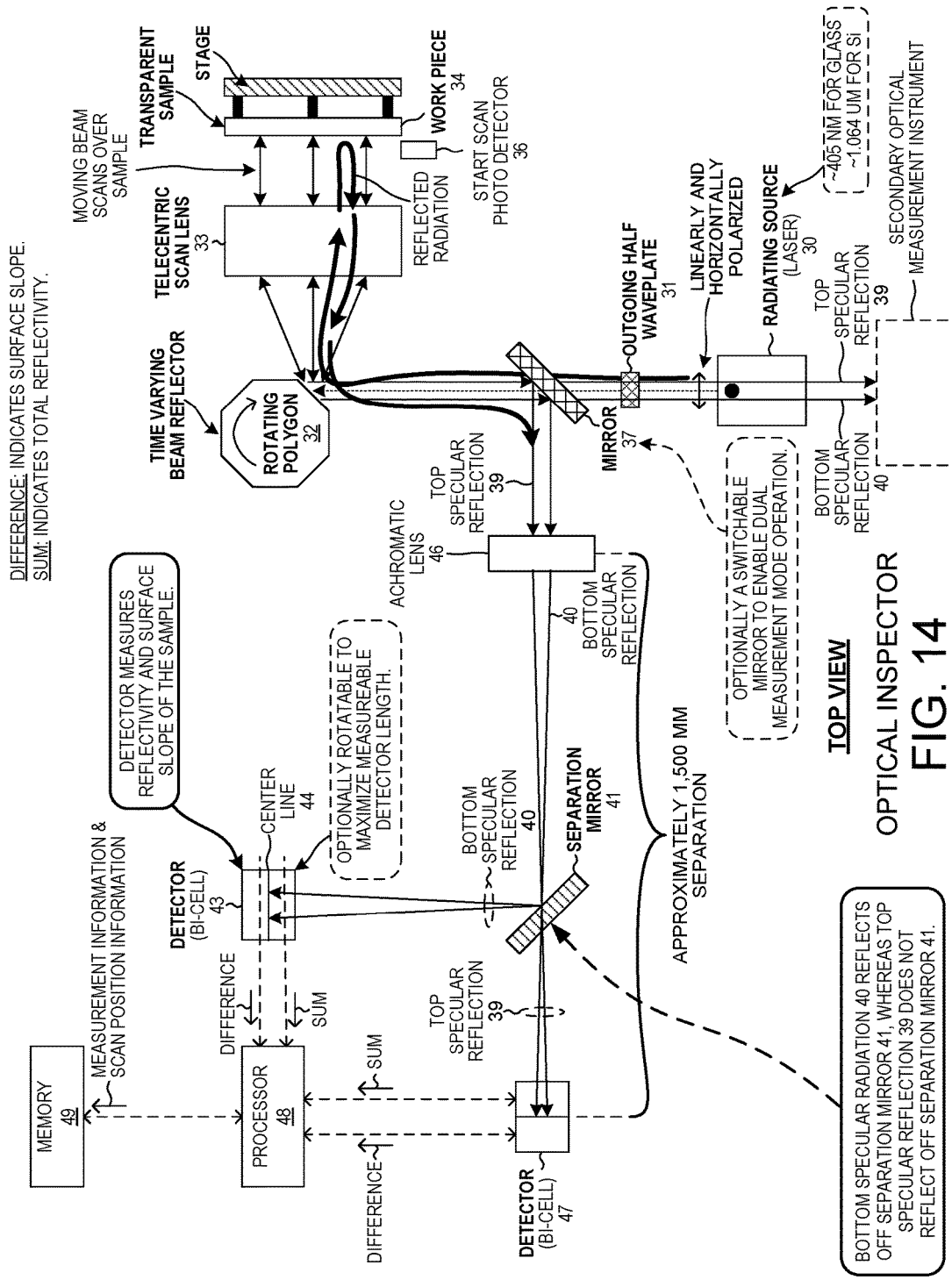
FIG. 14 is a top view diagram of a first optical inspector.

The bottom surface specular reflection 10 is reflected from the bottom surface of the work piece 2 at a similar angle to the scanning beam angle of incidence upon the bottom surface of the work piece 2. In the example of FIG. 2, the angle of incidence at the bottom surface of the work piece 2 is less than three degrees from normal and the angle of specular reflection through the work piece 2 is less than three degrees from normal in the opposite direction. When the bottom surface specular reflection exits the work piece 2 the angle of the bottom surface specular reflection 10 is redirected to three degrees from normal (similar to the top surface specular reflection 9). However, due to the additional distance traveled through the work piece at a non-zero angle, the location on the top surface of the work piece 2 at which the bottom surface specular reflection 10 exits the work piece 2 is different than the location where the top surface specular reflection 9 is reflected from the top surface of the work piece 2. The distance between these two locations is labeled "D" in FIG. 2. An example of an apparatus for measuring top surface specular reflection intensity and bottom surface specular reflection intensity is illustrated in FIG. 14.

Figure 3:
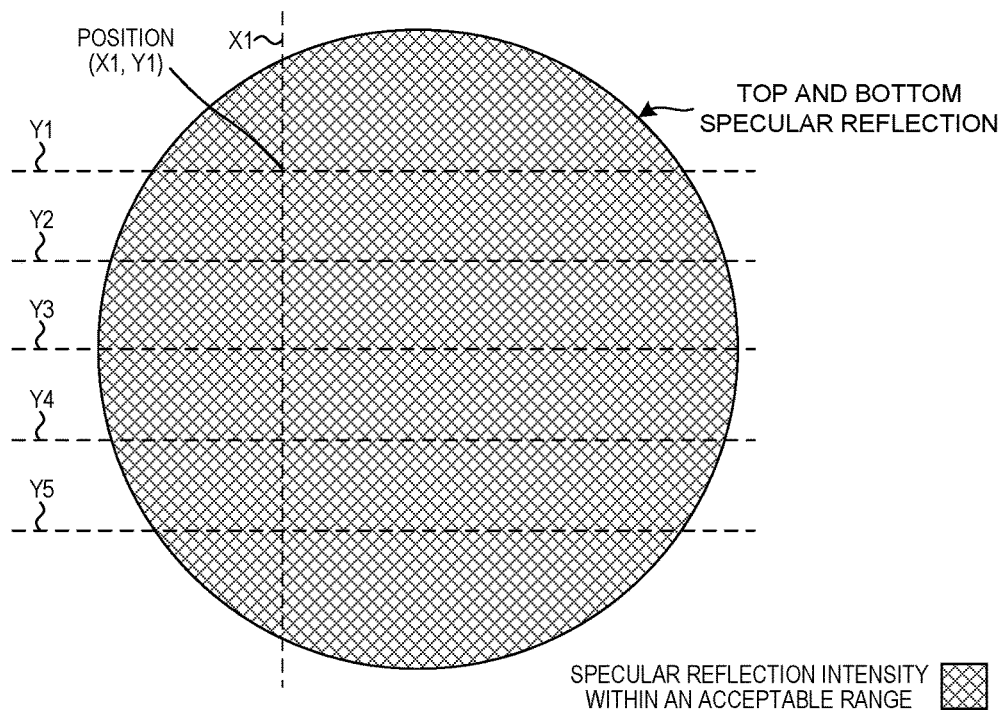
FIG. 3 is a specular reflection mapping illustrating the specular reflection resulting from the irradiation at position (X1, Y1).

FIG. 3 is a specular reflection mapping illustrating the top and bottom specular reflection resulting from the irradiation at position (X1, Y1) illustrated in FIG. 2. The top and bottom specular reflection mapping shows that no significant variation in measured specular reflection intensity is observed. More specifically, no significant variation in the top surface specular reflection intensity is observed and no significant variation in the bottom surface specular reflection intensity is observed. What is considered to be a "significant variation" is based on multiple factors. Such factors may include: the type of transparent sample being tested, the type of defect that is being detected, the frequency of the scanning beam 8, and the intensity of the scanning beam 8. In one example, it may be sufficient to determine that the measured specular reflection intensity is above a single threshold value. In another example, it may be sufficient to determine that the measured specular reflection intensity is below a single threshold value. In yet another example, it may be necessary to determine that the measured specular reflection intensity is within a specific range. These thresholds and ranges may be determined based on calculations describing variations of light reflections in the presence of various types of defects and setup conditions. Alternatively, threshold and ranges may be determined empirically by scanning a transparent sample with known defects and measuring the variations in specular reflection intensity caused by the known defects.

In one embodiment of the present invention, a scan of the transparent sample is first conducted, then a user defined set of thresholds or ranges are applied to determine the presence and location of a defect on the transparent sample. The defined set of thresholds and ranges can be adjusted to fine tune the detection of defects on a specific type of transparent sample under test.

The specular reflection intensities measured at position (X1, Y1) indicates that both the top surface specular reflection intensity and the bottom surface specular reflection intensity are within an acceptable range, which indicates that the work piece 2 does not have any defects at position (X1, Y1).

Figure 4:
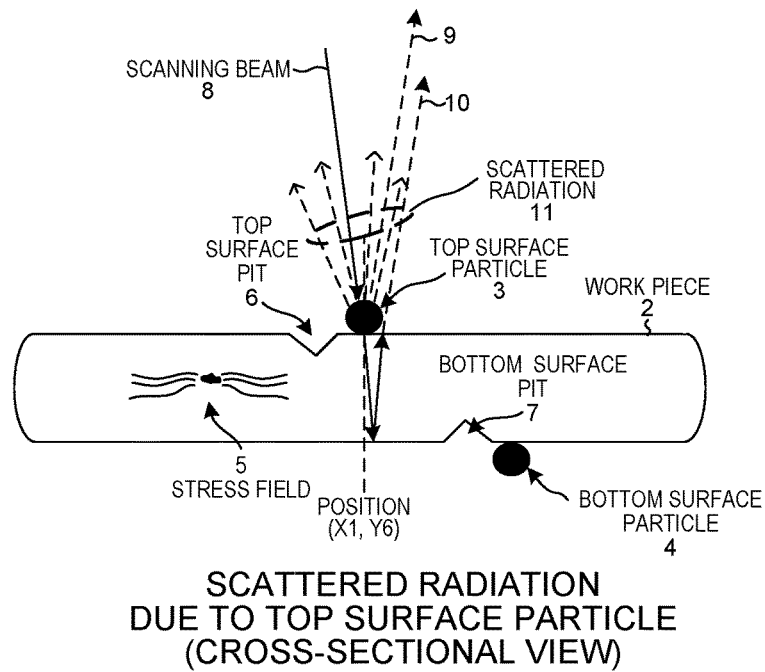
FIG. 4 is a cross-sectional diagram illustrating a scanning beam directed at position located at (X1, Y6) on the transparent sample, when a top surface particle is present at (X1, Y6).

FIG. 4 is a cross-sectional diagram illustrating the work piece 2 irradiated with a scanning beam 8 directed at position located at (X1, Y6). The scanning beam 8 is directed toward position (X1, Y6) on the top surface of the work piece 2. However, before irradiating the top surface of the work piece 2, the scanning beam 8 irradiates top surface particle 3 located at position (X1, Y6). Irradiation of top surface particle 3 causes scattered radiation 11. The scattered radiation 11 causes a decrease in top surface specular reflection 9 because the scattering of reflected light causes only a portion of the reflected light to travel along the path of top surface specular reflection 9. Irradiation of top surface particle 3 can also cause a decrease in bottom surface specular reflection 10 because a portion of the scanning beam 8 is blocked from entering the work piece 2 and does not reach the bottom surface of the work piece 2, therefore only a portion of the scattered radiation may radiate along the path of the bottom surface specular reflection 10. Thus, observation of a decrease in top surface specular reflection intensity and a decrease in bottom surface specular reflection intensity indicates that a defect is present at the top surface of work piece 2 at the scan location (X1, Y6). This defect detection logic is illustrated in the defect detection logic table shown in FIG. 17. An example of an apparatus for measuring top surface specular reflection intensity and bottom surface specular reflection intensity is illustrated in FIG. 14.

Figure 5:
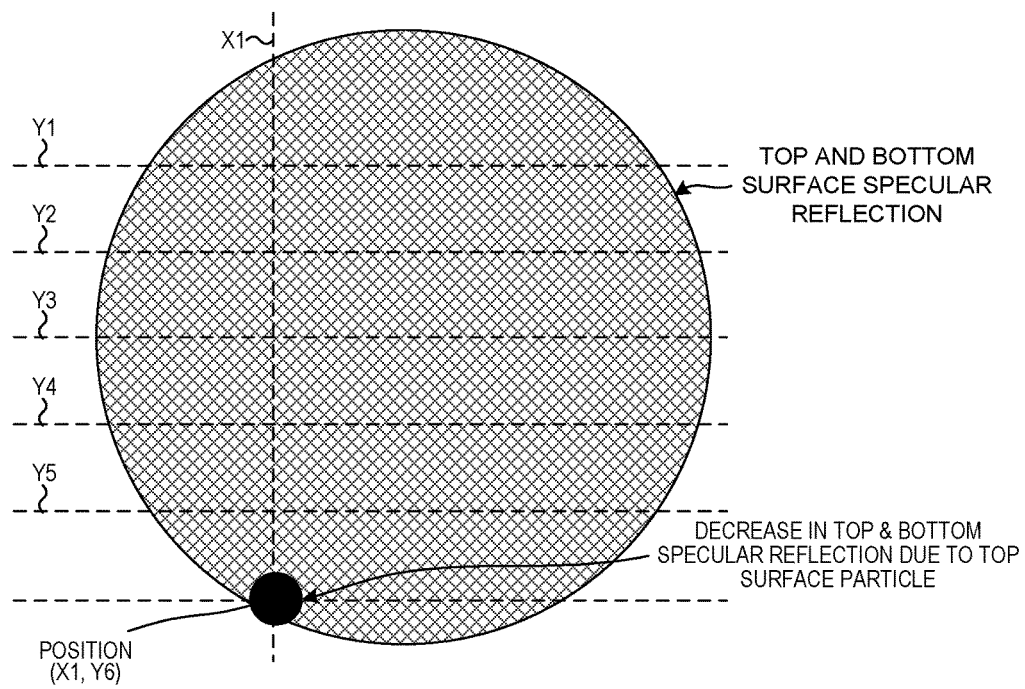
FIG. 5 is a specular reflection mapping illustrating the specular reflection resulting from the irradiation at position (X1, Y6).

FIG. 5 is a specular reflection mapping illustrating the top and bottom specular reflection resulting from the irradiation at position (X1, Y6) illustrated in FIG. 4. The top and bottom specular reflection mapping shows that significant variation in measured top and bottom surface specular reflection intensity is observed. More specifically, a decrease in both top surface specular reflection intensity and bottom surface specular reflection intensity is observed at position (X1, Y6). As discussed above, a decrease in top and bottom surface specular reflection indicates that a defect is present on the top surface of the work piece 2 at position (X1, Y6).

Figure 6:
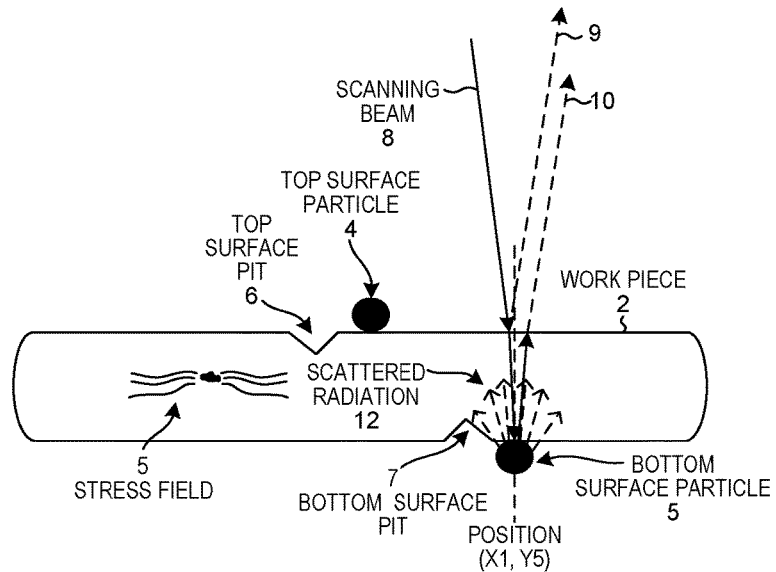
FIG. 6 is a cross-sectional diagram illustrating a scanning beam directed at position located at (X1, Y5) on the transparent sample, when a bottom surface particle is present at (X1, Y5).

FIG. 6 is a cross-sectional diagram illustrating the work piece 2 irradiated with a scanning beam 8 directed at position located at (X1, Y5). The scanning beam 8 irradiates position (X1, Y5) on the top surface of the work piece 2. A portion of scanning beam 8 is reflected by the top surface of the work piece 2 and causes top surface specular reflection 9 without significant intensity variation.

A portion of the scanning beam 8 is not reflected by the top surface of the work piece 2 and is redirected into the work piece 2 at an angle slightly closer to normal due to the change of the index of refraction of the work piece 2 from the index of refraction of air. The portion of the scanning beam 8 then irradiates the bottom surface of work piece 2. At the position of irradiation on the bottom surface of the work piece 2, a bottom surface particle 5 is present on the bottom surface of work piece 2. The presence of the bottom surface particle 5 causes scattered radiation 12. Scattered radiation 12 causes a decrease in bottom surface specular reflection because only a portion of the scattered radiation 12 radiates along the path of bottom surface specular reflection 10. Thus, observation of no significant decrease in top surface specular reflection and a decrease in bottom surface specular reflection indicates that a defect is present at the bottom surface of work piece 2 at the scan location (X1, Y5). This defect detection logic is illustrated in the defect detection logic table shown in FIG. 17. An example of an apparatus for measuring top surface specular reflection intensity and bottom surface specular reflection intensity is illustrated in FIG. 14.

Figure 7:
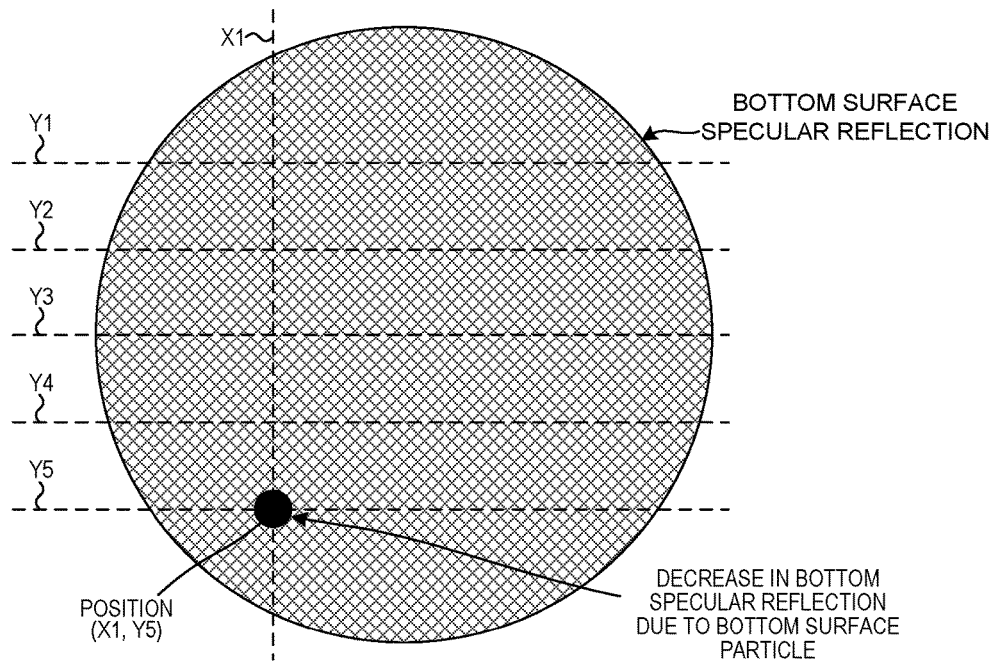
FIG. 7 is a specular reflection mapping illustrating the specular reflection resulting from the irradiation at position (X1, Y5).

FIG. 7 is a specular reflection mapping illustrating the bottom specular reflection resulting from the irradiation at position (X1, Y5) illustrated in FIG. 6. As mentioned above, there is no significant variation in the top surface specular reflection intensity. The bottom surface specular reflection mapping shows that significant variation in measured bottom surface specular reflection intensity is observed. More specifically, a decrease in bottom surface specular reflection intensity is observed at position (X1, Y5). As discussed above, the combination of no significant decrease in top surface specular reflection intensity and a decrease in bottom surface specular reflection intensity indicates that a defect is present on the bottom surface of the work piece 2 at position (X1, Y5).

Figure 8:
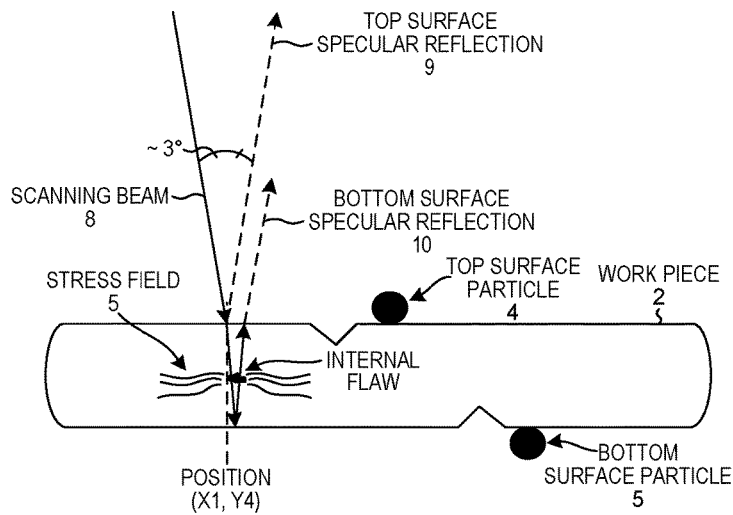
FIG. 8 is a cross-sectional diagram illustrating a scanning beam directed at position located at (X1, Y4) on the transparent sample, when an internal stress field is present at (X1, Y4).

FIG. 8 is a cross-sectional diagram illustrating the work piece 2 irradiated with a scanning beam 8 directed at position located at (X1, Y4). The scanning beam 8 irradiates position (X1, Y4) on the top surface of the work piece 2. A portion of scanning beam 8 is reflected by the top surface of the work piece 2 and causes top surface specular reflection 9 without significant intensity variation. The polarization of the top surface specular reflection is not significantly altered.

A portion of the scanning beam 8 is not reflected by the top surface of the work piece 2 and is redirected into the work piece 2 at an angle slightly closer to normal due to the change of the index of refraction of the work piece 2 from the index of refraction of air. The portion of the scanning beam 8 irradiates stress field 5. Stress field 5 can be caused by an internal flaw such as a crack, void, internal defect, or crystal slip line. Stress field 5 causes a change in the polarization of scanning beam 8. As a result the polarization of the bottom surface specular reflection 10 is different from the polarization of scanning beam 8. Stress field 5 may also cause a change in the amount of light reflected along the path of the bottom surface specular reflection 10 path.

Figure 9:
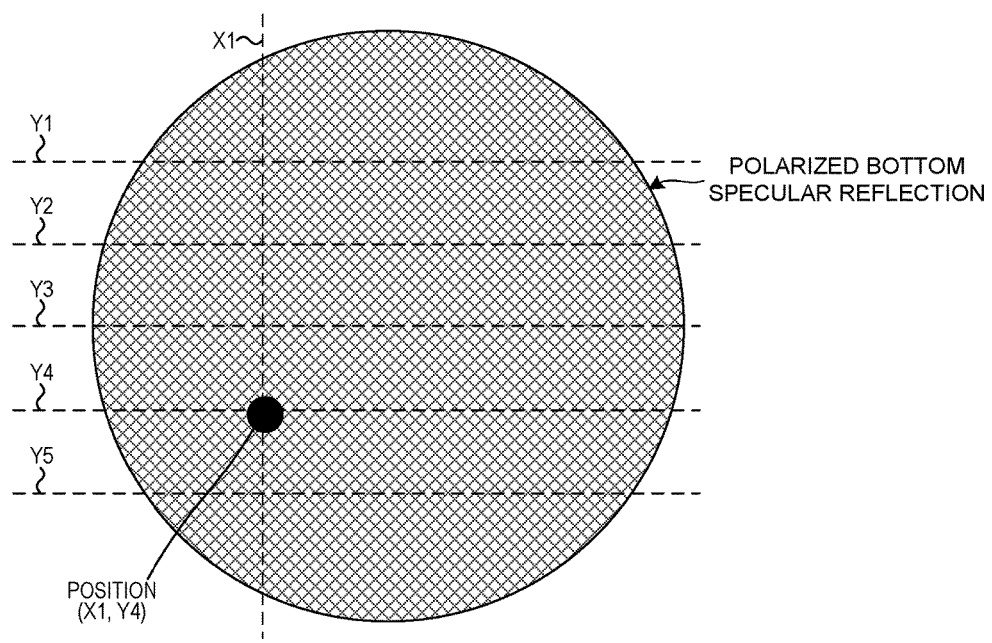
FIG. 9 is a specular reflection mapping illustrating the specular reflection resulting from the irradiation at position (X1, Y4).
Figure 15:
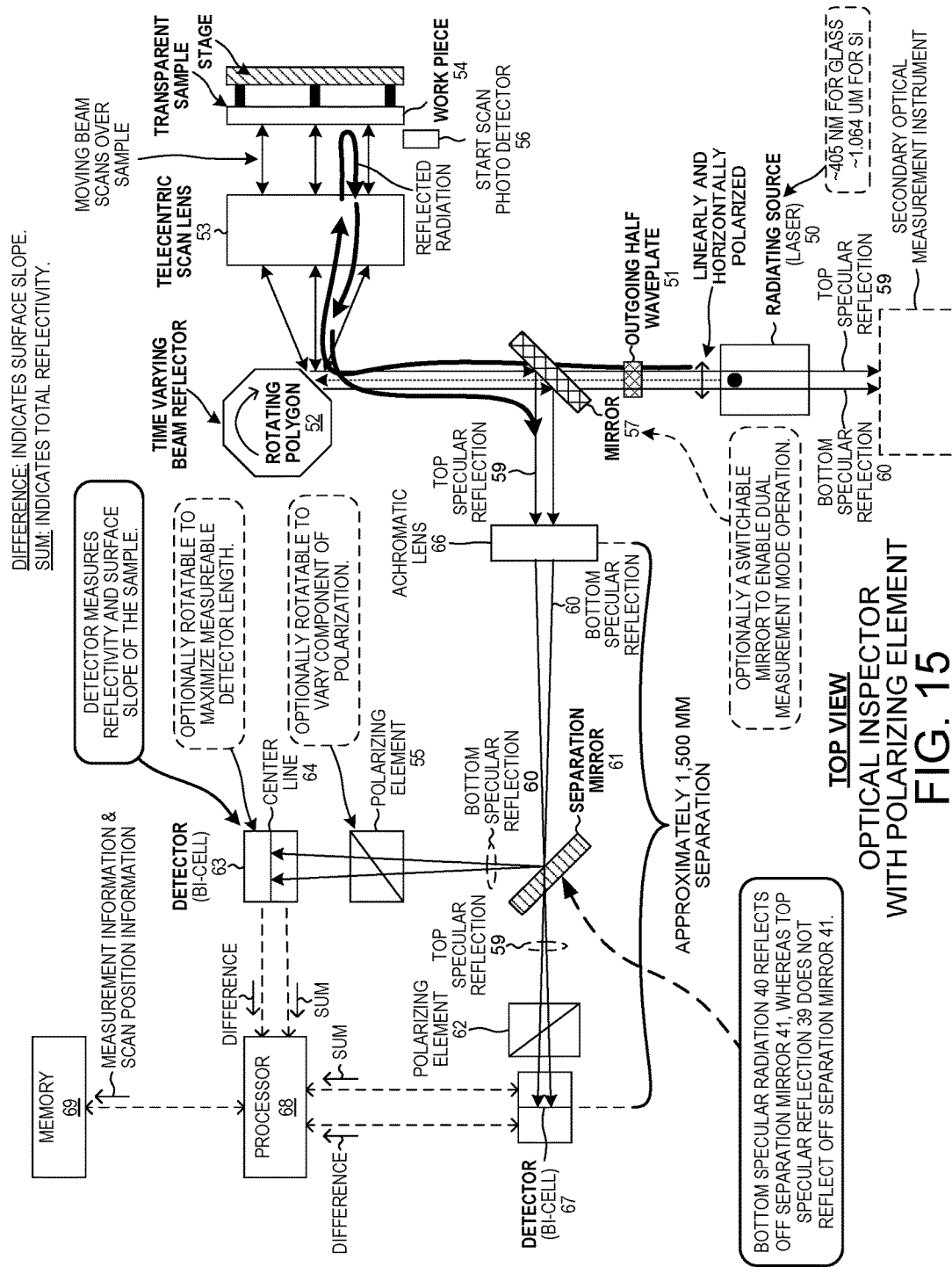
FIG. 15 is a top view diagram of a second optical inspector with a polarizing element.

FIG. 9 is a polarized specular reflection mapping illustrating the bottom specular reflection resulting from the irradiation at position (X1, Y4) illustrated in FIG. 8. Polarized specular reflection is measured using a polarizing element that only allows selected components of polarization to pass through the polarizing element before the specular reflection intensity is measured. An example of an apparatus for measuring polarized top surface specular reflection intensity and polarized bottom surface specular reflection intensity is illustrated in FIG. 15. In some instances, the internal defect may result in a dipole shape on the polarized bottom surface specular reflection mapping.

As mentioned above, there is no significant variation in the top surface specular reflection intensity or the top surface specular reflection polarization. The polarized bottom surface specular reflection mapping shows that significant variation in measured polarized bottom surface specular reflection intensity is observed. In one example, a decrease in polarized bottom surface specular reflection intensity is observed at position (X1, Y4). In another example, an increase in polarized bottom surface specular reflection intensity is observed at position (X1, Y4). A change in the polarization of the bottom surface specular reflection can cause both an increase and a decrease in measured bottom surface specular reflection intensity because depending on the configuration of the polarizing element, the change in the polarization of the bottom surface specular reflection can cause the polarization of the bottom surface specular reflection to become more or less aligned with the polarizing element. When the polarization of the bottom surface specular reflection becomes more aligned with the polarizing element, more of the bottom surface specular reflection will be measured. When the polarization of the bottom surface specular reflection becomes less aligned with the polarizing element, less of the bottom surface specular reflection will be measured. The combination of no significant decrease in top surface specular reflection intensity and a significant change in polarized bottom surface specular reflection intensity indicates that a defect is present inside work piece 2 at position (X1, Y4). The logic of this determination is illustrated in defect detection logic tables shown in FIGS. 17 and 18.

Figure 10:
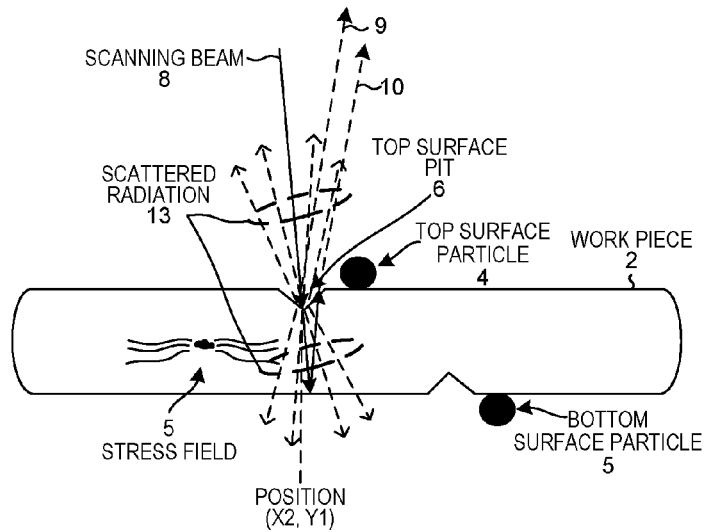
FIG. 10 is a cross-sectional diagram illustrating a scanning beam directed at position located at (X2, Y1) on the transparent sample, when a top surface pit is present at (X2, Y4).

FIG. 10 is a cross-sectional diagram illustrating the work piece 2 irradiated with a scanning beam 8 directed at position located at (X2, Y1). Work piece 2 has a top surface pit 6 defect located at position (X2, Y1). Irradiation of top surface pit 6 causes scattered radiation 13. The scattered radiation 13 causes a decrease in top surface specular reflection 9 because the scattering of reflected light causes only a portion of the reflected light to travel along the path of top surface specular reflection 9. Irradiation of top surface pit 6 also cases a decrease in bottom surface specular reflection 10 because the portion of scanning beam 8 that enters the work piece 2 is scattered, therefore the only a portion of the scattered radiation reflects from the bottom surface of the work piece 2 along the path of the bottom surface specular reflection 10. Thus, observation of a decrease in top surface specular reflection and a decrease in bottom surface specular reflection indicates that a defect is present at the top surface of work piece 2 at the scan location (X2, Y1). This defect detection logic is illustrated in the defect detection logic table shown in FIG. 17. An example of an apparatus for measuring top surface specular reflection intensity and bottom surface specular reflection intensity is illustrated in FIG. 14.

Figure 11:
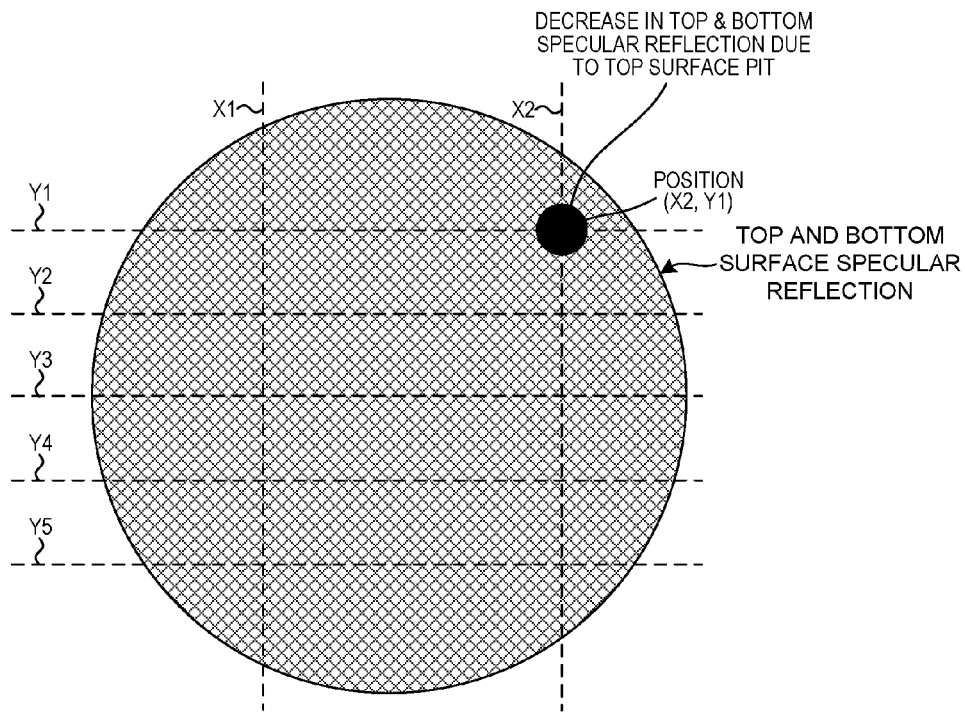
FIG. 11 is a specular reflection mapping illustrating the specular reflection resulting from the irradiation at position (X2, Y1).

FIG. 11 is a specular reflection mapping illustrating the top and bottom specular reflection resulting from the irradiation at position (X2, Y1) illustrated in FIG. 10. The top and bottom specular reflection mapping shows that significant variation in measured top and bottom surface specular reflection intensity is observed. More specifically, a decrease in top and bottom surface specular reflection intensity is observed at position (X2, Y1). As discussed above, a decrease in top and bottom surface specular reflection indicates that a defect is present on the top surface of the work piece 2 at position (X2, Y1).

Figure 12:
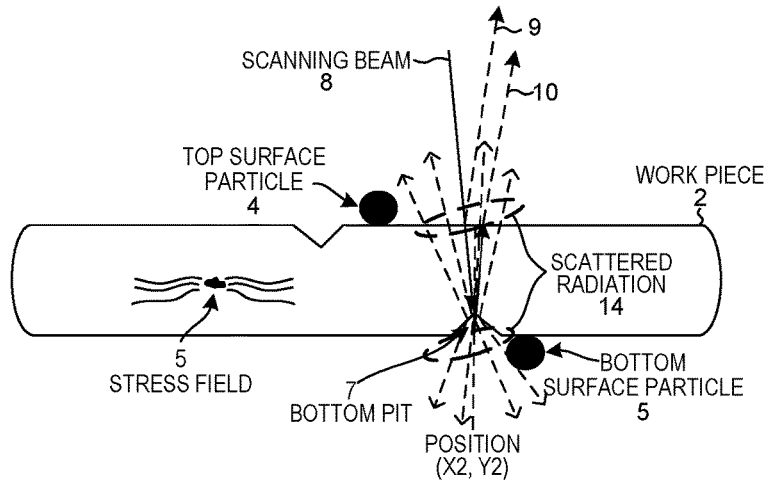
FIG. 12 is a cross-sectional diagram illustrating a scanning beam directed at position located at (X2, Y2) on the transparent sample, when a bottom surface pit is present at (X2, Y4).

FIG. 12 is a cross-sectional diagram illustrating the work piece 2 irradiated with a scanning beam 8 directed at position located at (X2, Y2). Work piece 2 has a bottom surface pit 7 defect located at position (X2, Y2). Irradiation of the top surface at position (X2, Y2) causes top surface specular reflection intensity with no significant variation. A portion of scanning beam 8 enters work piece 2 and irradiates the bottom surface pit 7. Irradiation of bottom surface pit 7 causes scattered radiation 14. The scattered radiation 14 causes a decrease in bottom surface specular reflection 10 because the scattering of reflected light causes only a portion of the reflected light to travel along the path of bottom surface specular reflection 10. Irradiation of bottom surface pit 7 does not significantly affect the top surface specular reflection intensity. Thus, observation of no significant variation in top surface specular reflection intensity and a decrease in bottom surface specular reflection intensity indicates that a defect is present at the bottom surface of work piece 2 at the scan location (X2, Y2). This defect detection logic is illustrated in the defect detection logic table shown in FIG. 17. An example of an apparatus for measuring top surface specular reflection intensity and bottom surface specular reflection intensity is illustrated in FIG. 14.

Figure 13:
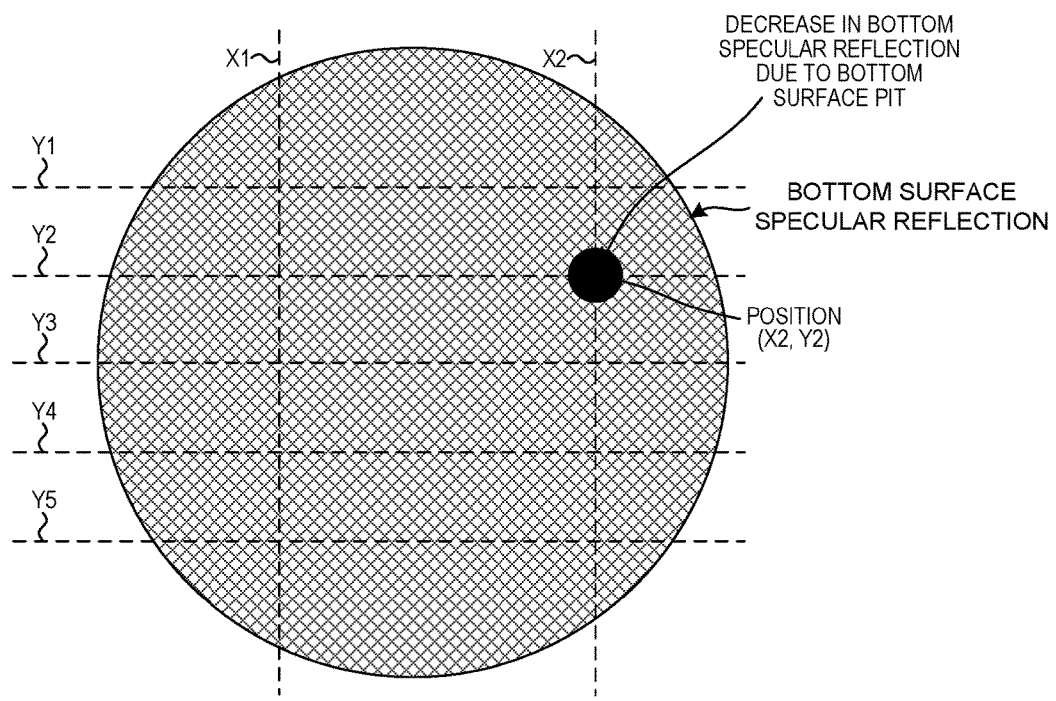
FIG. 13 is a specular reflection mapping illustrating the specular reflection resulting from the irradiation at position (X2, Y2).

FIG. 13 is a specular reflection mapping illustrating the bottom specular reflection resulting from the irradiation at position (X2, Y2) illustrated in FIG. 12. As mentioned above, the bottom surface pit 7 does not cause a significant change in the top surface specular reflection intensity. The bottom specular reflection mapping shows that significant variation in measured bottom surface specular reflection intensity is observed. More specifically, a decrease in bottom surface specular reflection intensity is observed at position (X2, Y2). As discussed above, no significant variation in top surface specular reflection intensity and a decrease in bottom surface specular reflection intensity indicates that a defect is present on the bottom surface of the work piece 2 at position (X2, Y2).

FIG. 14 is a top view diagram of an optical inspector. The optical inspector includes a radiating source 30, an outgoing half waveplate 31, a time varying beam reflector (rotating polygon 32), a telecentric scan lens 33, a start of scan detector 36, a first mirror 37, a focusing lens 46, a separation mirror 41, a first photo detector 43, a second detector 47, a processor 48, and a memory 49. It is noted herein, the use of rotating polygon is exemplary. Any time varying beam reflector, such as a resonant galvanometer, a rotating double sided mirror, or acousto-optic beam deflector can be utilized as well.

The radiating source 30 irradiates outgoing half waveplate 31 with a source beam. In one example, the radiating source 30 is a laser. Outgoing half waveplate 31 allows the linear polarization of laser to be rotated to a desired angle. The rotated linearly polarized beam is directed by the rotating polygon 32 to a first location on the telecentric scan lens 33. The angle at which the source beam approaches the telecentric scan lens 33 depends upon the angle of rotation of the rotating polygon 32 when the source beam contacts the rotating polygon 32. However, regardless of the angle at which the source beam approaches the telecentric scan lens 33, the telecentric scan lens 33 directs the source beam to a work piece 34 at an angle that is substantially normal to the surface of the work piece 34. In one example, the work piece 34 is the transparent sample (work piece 2) shown in FIG. 1 and the telecentric scan lens 33 directs the source beam to the work piece 34 at an angle of approximately three degrees from normal.

The source beam directed, at a substantially normal angle, to the work piece 34 generates a reflection of the source beam. A first portion of the reflected source beam is specular reflection. A second portion of the reflected source beam is near specular scattered radiation. Specular reflection is the mirror-like reflection of light from a surface, in which light from a single incoming direction is reflected into a single outgoing direction (in adherence with the law of reflection). Near specular scattered radiation is light which is scattered (or deflected) by defects in a region which is just outside the profile of the specular beam. Measuring both the specular reflection and the near specular scattered radiation allows the detection of defects which may not be visible in the specular reflection alone. Near specular scattered radiation is referred to as scatter radiation herein.

As discussed above, the specular reflection includes top surface specular reflection and bottom surface specular reflection from the transparent sample (work piece 34). The reflected radiation, including top surface specular reflection 39 and bottom surface specular reflection 40, is reflected back to the telecentric scan lens 33. The telecentric scan lens 33 directs the top surface specular reflection 39 and the bottom surface specular reflection 40 to the rotating polygon 32. The rotating polygon 32 directs the top surface specular reflection 39 and bottom surface specular reflection 40 back toward the radiating source 30. At this point, separating the source beam from the reflected light would be impractical if both the source beam and the reflected beams were traveling in the same space. To avoid this problematic situation, the radiating source 30 is placed at a location at an offset from the central axis of the telecentric scan lens 33. This directs the reflected radiation away from the radiating source 30 without altering the source beam radiating from the radiating source 30.

Figure 21:
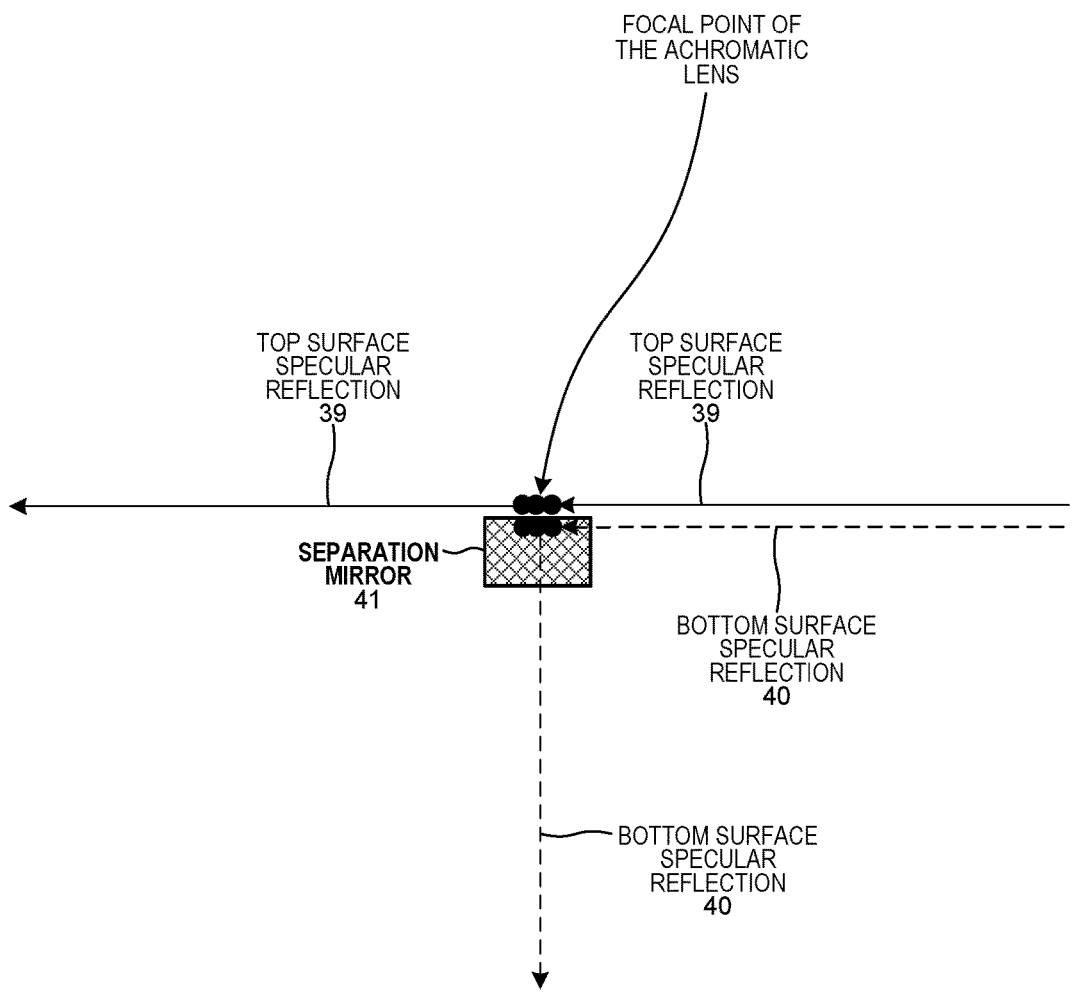
FIG. 21 is a diagram illustrating the position and functionality of a separation mirror.

Mirror 37 reflects both top surface specular reflection 39 and bottom surface specular reflection 40 to focusing lens 46. Focusing lens 46 focuses both the top surface specular reflection 39 and the bottom surface specular reflection 40 to a focal point. In one example, the focusing lens 46 is an achromatic lens. Separation mirror 41 is located approximately at the focal point of focusing lens 46. Examples of various shapes of the separation mirror are shown in FIG. 16. At this point of focus, the top surface specular reflection 39 is physically separated from the bottom surface specular reflection 40. This separation is illustrated in FIG. 21. The separation mirror 41 is positioned to reflect the bottom surface specular reflection 40 while not affecting the propagation of top surface specular reflection 39. Separation mirror 41 reflects the bottom surface specular reflection 40 toward detector 43 while allowing top surface specular reflection 39 to continue to detector 47. Thus, detector 43 is irradiated by the bottom surface specular reflection 40 and detector 47 is irradiated by top surface specular reflection 39.

The detector 43 is located such that the bottom surface specular reflection 40 should irradiate the center of detector 43. In one example, detector 43 is a bi-cell detector. In this example, the bottom surface specular reflection irradiates the bi-cell detector 43 on the center line 44 between the two photodiodes included in the bi-cell detector 43. In the event that the bottom surface slope (the "micro-waviness") of the work piece is not normal to the source beam, the resulting bottom surface specular reflection 40 will deviate from the center line 44. A deviation from the center line 44 will cause a greater amount of the bottom surface specular reflection 40 to irradiate one of the two photodiodes in the bi-cell detector 43. In response, the bi-cell detector 43 will output an increased difference value indicating a change in the slope of the bottom surface of the work piece 34. A negative difference value indicates a slope varying in a first direction. A positive difference value indicates a slope varying in a second direction. The slope measured is the surface slope of the bottom surface of the work piece 2 in direction perpendicular to the optical scan line. Regardless of the deviation of the bottom surface specular reflection 40 from the center line 44, the bi-cell detector 43 will output a sum value indicating the intensity of the bottom surface specular reflection 40 from work piece 34. For additional information regarding measurement of surface slope, see: U.S. patent application Ser. No. 13/861,383 (U.S. Pat. No. 8,848,181) entitled "MULTI-SURFACE SCATTERED RADIATION DIFFERENTIATION" filed on Apr. 12, 2013 (the entire subject matter of which is incorporated herein by reference).

The detector 47 is located such that the top surface specular reflection 39 should irradiate the center of detector 47. In one example, detector 47 is a bi-cell detector. In this example, the top surface specular reflection irradiates the bi-cell detector 47 on the center line between the two photodiodes included in the bi-cell detector 47. In the event that the top surface slope (the "micro-waviness") of the work piece is not normal to the source beam, the resulting top surface specular reflection 39 will deviate from the center line. A deviation from the center line will cause a greater amount of the top surface specular reflection 39 to irradiate one of the two photodiodes in the bi-cell detector 47. In response, the bi-cell detector 47 will output an increased difference value indicating a change in the slope of the top surface of the work piece 34. A negative difference value indicates a slope varying in a first direction. A positive difference value indicates a slope varying in a second direction. The slope measured is the surface slope of the top surface of the work piece 2 in direction perpendicular to the optical scan line. Regardless of the deviation of the bottom surface specular reflection 39 from the center line, the bi-cell detector 47 will output a sum value indicating the intensity of the top surface specular reflection 39 from work piece 34.

In one embodiment, the radiating source is a four hundred and five nanometer laser and the work piece is glass. In another embodiment, the radiating source is a one thousand and sixty-four nanometer laser and the work piece is silicon.

In another embodiment, detector 43 is rotatable about the optical axis of the bottom surface specular reflection 40 and detector 47 is rotatable about the optical axis of the top surface specular reflection 39.

In yet another embodiment, the optical path length between the focusing lens and the first detector is approximately one-thousand, five-hundred millimeters.

In one example, a processor 48 is also included in the top and bottom surface optical inspector shown in FIG. 14. The processor 48 receives a difference output signal from bi-cell detector 43, a sum output signal from bi-cell detector 43, a difference output signal from bi-cell detector 47, and a sum output signal from bi-cell detector 47. In response, processor 48 determines: if defects are present at the scan location on the work piece 34, if the defect is located on the top surface of the work piece 34, if the defect is located on the bottom surface of the work piece 34, and if the defect is located internal to the work piece 34.

The processor may also communicate with a motor controlling rotating polygon 32. The processor may increase or decrease the rate of rotation of the rotating polygon 32. For example, when switching from using a high-bandwidth detector to a low-bandwidth detector, it may be required that the rate of rotation of the rotating polygon 32 be decreased. Alternatively, when switching from using a low-bandwidth detector to a high-bandwidth detector, it may be necessary to increase the rate of rotation of the rotating polygon 32.

In another example, memory 49 is included in the top and bottom surface optical inspector shown in FIG. 14. Memory 49 stores information output by processor 48. (i.e. defect location information, or defect indicator information). Memory 49 also stores location information indicating the location on the work piece which was scanned to measure the defect information or defect indicator information. Defect information includes a status as to whether the scanned location on the work piece contains a defect and on which surface the defect present at the location. Defect indicator information includes various measurements from the scanned location on the work piece (i.e. top surface slope, bottom surface slope, top surface specular reflection intensity, and bottom surface specular reflection intensity).

In one example, the scan of the work piece is done with the polygon rotating at a high speed and the data sampling of the bi-cell detector is run at approximately 16 MHz with the radiating source running at full intensity. Since the rotating polygon can rotate at high speeds, an entire 100 mm diameter work piece can be measured in about ten seconds.

In another example, the rotating polygon begins to spin upon power up of the device and continues to spin until the entire device is powered off. The constant spinning of the rotating polygon during operation is beneficial in that spin-up and spin-down delay time is eliminated during regular operation. The work piece is moved in one direction (not shown) by a precision stage to make a map of the entire work piece surface. In one embodiment, shown in FIG. 14, the optical inspector includes a start of scan photodetector 36 which is placed at the edge of the scan line and serves to trigger the acquisition of data sampling when the scanned beam passes over the detector 36.

This above process is repeated as the work piece 34 is moved underneath the optical inspector. A precision stage controller directs the movement of the work piece 34 during the inspection process. In one example, the processor 48 outputs defect inspection data which is logged along with the work piece scan location. The number and location of defects on the work piece will determine the disposition of the work piece. In one example, depending upon the location and type of defect, some portions of the work piece may be useful and others portions of the work piece may be discarded. In another example, if the work piece has many defects then the entire work piece may be discarded.

It is noted herein, that bi-cell detectors 43 and 47 are of exemplary use in this disclosure. One skilled in the art will readily realize that the bi-cell detectors 43 and 47 may be replaced with various multi-cell detectors to achieve the utility of the present invention.

In another embodiment, mirror 37 is a switchable mirror that can be adjusted to not reflect the top and bottom surface specular reflections 39 and 40. A switchable mirror 37 allows for a single optical inspector including two different optical measurement instruments to select between the use of either optical measurement instrument by simply switching the position of mirror 37.

FIG. 15 is a top view diagram of an optical inspector with a polarizing element. The optical inspection illustrated in FIG. 15 performs a similar fashion as the optical inspector illustrated in FIG. 14, but at least one polarizing element to control the components of polarization that irradiate a detector.

In one example, the optical inspector includes a single polarizing element 55 that controls the components of polarization that irradiate detector 63. As discussed above regarding FIGS. 8 and 9, setting the rotational angle of the polarizing element allows only one component of polarization of bottom surface specular reflection to irradiate detector 63. This allows detector 63 to measure changes in polarization of the bottom surface specular reflection due to a stress field in a work piece. For example, when the scanning beam travels through a stress field, the polarization of the bottom surface specular reflection is altered, which can cause an increase or decrease in the amount of light that will pass through the polarizing element.

In another example, the optical inspector includes a single polarizing element 62 that controls the components of polarization that irradiate detector 67. Setting the rotational angle of the polarizing element to only allow one component of polarization of the top surface specular reflection to irradiate detector 67 allows detector 67 to measure changes in polarization of the top surface specular reflection due to a surface defect in a work piece. For example, when the scanning beam travels through a top surface stain, the polarization of the top surface specular reflection is altered, which can cause an increase or decrease in the amount of light that will pass through the polarizing element.

In yet another embodiment, the optical inspector includes two polarizing elements 55 and 62. Polarizing element 55 controls the components of polarization that irradiate detector 63. As discussed above regarding FIGS. 8 and 9, setting the rotational angle of the polarizing element to only allow one component of polarization of bottom surface specular reflection to irradiate detector 63 allows detector 63 to measure changes in polarization of the bottom surface specular reflection due to a stress field in a work piece. For example, when the scanning beam travels through a stress field, the polarization of the bottom surface specular reflection is altered, which can cause an increase or decrease in the amount of light that will pass through the polarizing element.

Polarizing element 62 controls the components of polarization that irradiate detector 67. Setting the rotational angle of the polarizing element to only allow one component of polarization of the top surface specular reflection to irradiate detector 67 allows detector 67 to measure changes in polarization of the top surface specular reflection due to a surface defect in a work piece. For example, when the scanning beam travels through a top surface stain, the polarization of the top surface specular reflection is altered, which can cause an increase or decrease in the amount of light that will pass through the polarizing element.

Use of a polarizing element allows the optical inspector to detect defects such as: stress fields caused by internal flaws, top and bottom surface stains, top and bottom surface cracks, and top and bottom surface scratches. In each of these defect situations, the polarization of the specular reflection is altered by the defect. Therefore, utilization of an optical inspector with a polarizing element as disclosed in FIG. 15 allows detection of the presence of these types of defects on either the top, bottom or internal to the work piece.

As discussed in above, either of the two defect detection tables shown in FIGS. 17 and 18 can be used to determine the surface location of a defect. For some types of defects it may be sufficient to only determine if a decrease below a threshold value in specular reflection intensity occurred in the top surface specular reflection intensity (shown in FIG. 17). For other types of defects it may be necessary to determine if a decrease below a threshold value in specular reflection intensity occurred in both the top surface specular reflection intensity and the bottom surface specular reflection intensity. The threshold value for the top surface specular reflection intensity may be different from the threshold value for the bottom surface specular reflection intensity.

In other situations, it may be sufficient to only determine if an increase above a threshold value in specular reflection intensity occurred in the top surface specular reflection intensity (not shown). Alternatively, it may be necessary to determine if an increase above a threshold value in specular reflection occurred in both the top surface specular reflection intensity and the bottom surface specular reflection intensity. The threshold value for the top surface specular reflection intensity may be different from the threshold value for the bottom surface specular reflection intensity.

It may also be useful to determine if the measured specular reflection intensity is within a specific range of specular reflection intensities (shown in FIG. 18). A first range of specular reflection intensity values may be defined for top surface specular reflection intensity and a second range of specular reflection intensity values may be defined for bottom surface specular reflection intensity.

Figure 19:
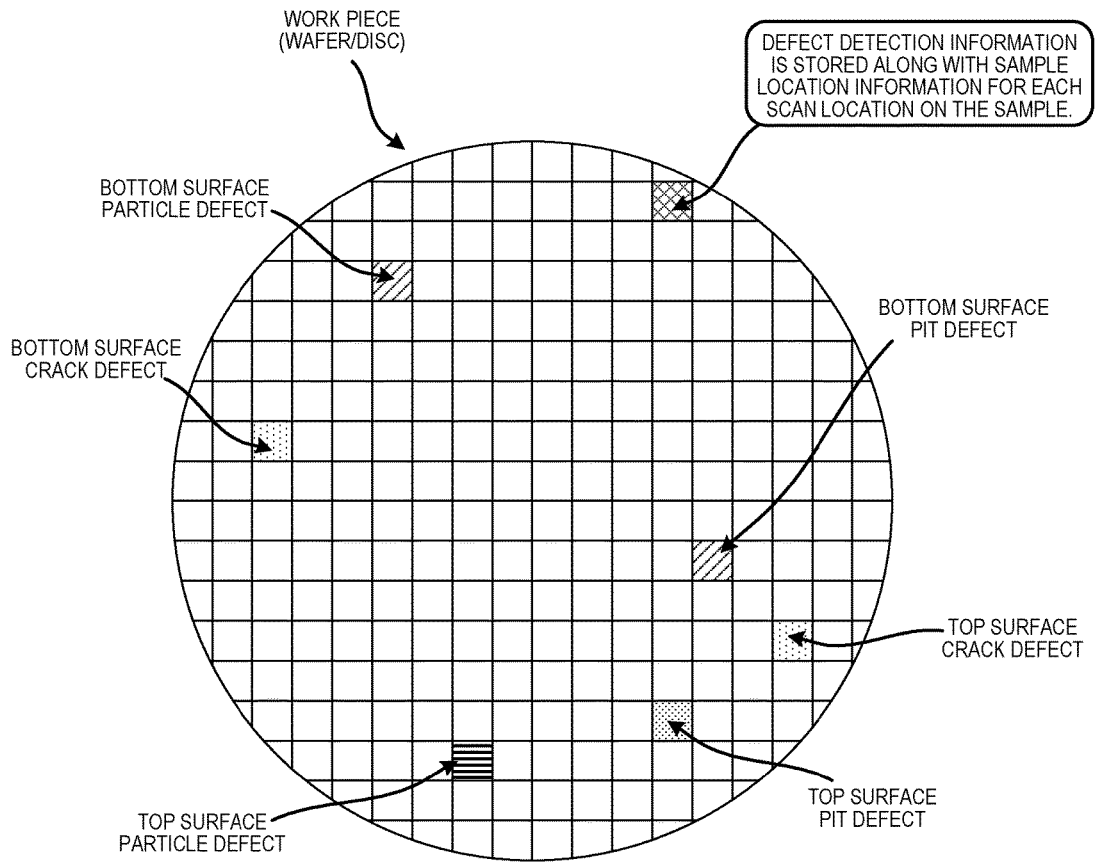
FIG. 19 illustrates a result work piece defect mapping that is generated by applying the logic described in the table of FIG. 17 to measurements measured across the surface of the work piece.

FIG. 19 illustrates a result work piece defect mapping that is generated by applying the logic described in the table of FIGS. 17 and 18 to measurements measured across the surface of the work piece. The work piece defect mapping can be used by work piece manufacturers to identify the parts of the work piece that are not to have additional processing so as to not waste resources and further develop a portion of the work piece that is defective.

Figure 20:
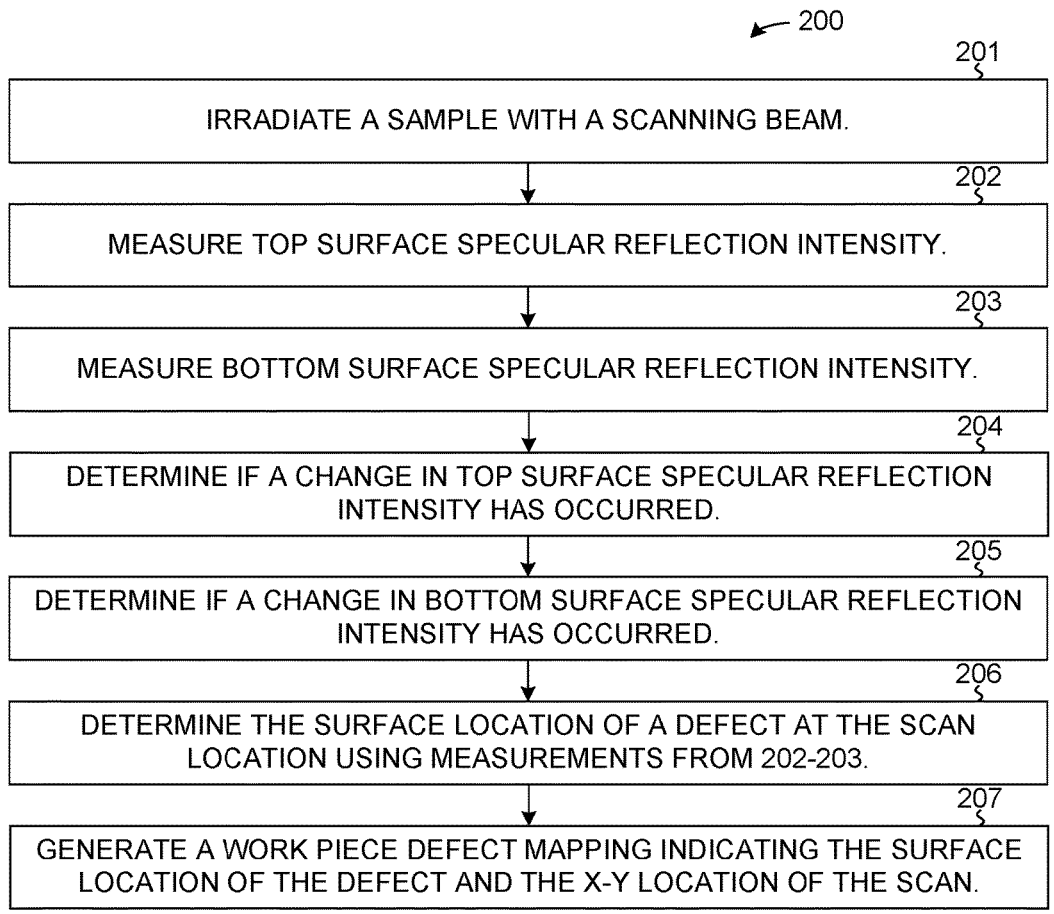
FIG. 20 is a flowchart 200 illustrating the steps included in a defect detection process.

FIG. 20 is a flowchart 200 illustrating the steps included in the defect detection process. In step 201, the work piece is irradiated with a scanning beam. In step 202, top surface specular reflection intensity is measured. In step 203, bottom surface specular reflection intensity is measured. In step 204, it is determined if a significant change in top surface specular reflection intensity has occurred. In step 205, it is determined if a significant change in bottom surface specular reflection intensity has occurred. In one example, steps 202 through 205 are performed simultaneously. In step 206, the presence of a defect and the surface on which the defect is located is determined using the measurements taken in steps 202 through 205. In step 207, the surface location of the defect determined in step 206 and the scanning location on the work piece is used to generate a work piece defect mapping.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method for detecting defects, comprising:
    (a) directing a scanning beam to a first location on a first surface of a transparent sample, wherein a portion of the scanning beam irradiates a second surface of the transparent sample;
    (b) at the first location, measuring top surface specular reflection intensity, wherein the top surface specular reflection intensity results from irradiation by the scanning beam at the first location on the first surface of the transparent sample;
(c) storing coordinate values of the first location and the measured top surface specular reflection intensity in a memory;
(d) comparing the top surface specular reflection intensity measured with an expected top surface specular reflection intensity value; and
(e) determining that a defect is present on the top surface of the transparent sample when the measured top surface specular reflection intensity is less than the expected top surface specular reflection intensity value.

2. The method of claim 1, further comprising:
(f) measuring bottom surface specular reflection intensity;
(g) comparing the measured bottom surface specular reflection intensity with an expected bottom surface specular reflection intensity value; and
(h) determining that a defect is present at bottom surface of the transparent sample when the top surface specular reflection intensity is equal to or greater than the expected top surface specular reflection intensity value and the bottom surface specular reflection intensity is less than the expected bottom surface specular reflection intensity value.

3. The method of claim 2, further comprising:
(i) repeating steps (a) through (h) at a plurality of locations on the first surface of the first transparent sample.

4. The method of claim 1, wherein the defect is one selected from the group consisting of: (1) a top surface particle, (2) a bottom surface particle, (3) a bottom surface pit, (4) a top surface pit, (5) a top surface scratch, (6) a bottom surface scratch, (7) a top surface stain, (8) a bottom surface stain, (9) an internal crack, (10) an internal stress field, (11) an internal void, or (12) an internal defect.

5. The method of claim 1, wherein the transparent sample is one selected from a group comprising, glass, plastic, quartz, sapphire, silicon, Silicon Carbide (SiC), and Gallium Nitride (GaN).

6. The method of claim 1, wherein the directing of the scanning beam to the first location on the first surface of the transparent sample is performed, at least in part, by a radiating source, a rotating polygon, and a telecentric scan lens.

7. The method of claim 1, further comprising:
(f) measuring top surface slope at the first location, wherein the measuring of top surface slope is performed, at least in part, by an achromatic lens and a bi-cell detector.

8. The method of claim 1, further comprising:
(f) measuring bottom surface slope at the first location, wherein the measuring of bottom surface slope is performed, at least in part, by an achromatic lens, and a bi-cell detector.

9. A method for detecting defects, comprising:
(a) directing a scanning beam to a first location on a first surface of a transparent sample, wherein a portion of the scanning beam irradiates a second surface of the transparent sample;
(b) at the first location, measuring top surface specular reflection intensity, wherein the top surface specular reflection intensity result from irradiation by the scanning beam at the first location on the first surface of the transparent sample;
(c) storing coordinate values of the first location and the measured top surface specular reflection intensity in a memory;
(d) determining if the measured top surface specular reflection intensity is within a first intensity range, wherein the first intensity range includes an expected top surface specular reflection intensity value; and
(e) determining that a defect is present on the top surface of the transparent sample when the measured top surface specular reflection intensity is not within the first intensity range.

10. The method of claim 9, further comprising:
(f) repeating steps (a) through (e) at a plurality of locations on the first surface of the first transparent sample.

11. The method of claim 9, further comprising:
(f) at the first location, measuring bottom surface specular reflection intensity;
(g) comparing the measured bottom surface specular reflection intensity with a second intensity range;
(h) determining if the measured bottom surface specular reflection intensity is within a second intensity range, wherein the second intensity range includes an expected bottom surface specular reflection intensity value; and
(i) determining that a defect is present on the bottom surface of the transparent sample when the measured top surface specular reflection intensity is within the first intensity range and the measured bottom surface specular reflection is not within the second intensity range.

12. The method of claim 9, wherein the top surface specular reflection passes through a second polarizing element before the measurement of the top surface specular reflection intensity.

13. The method of claim 9, wherein the defect is selected from the group consisting of: (1) a top surface crack, (2) a bottom surface crack, (3) an internal stress field, (4) an internal void, or (5) an internal defect.

14. The method of claim 9, wherein the directing of the scanning beam to the first location on the first surface of the transparent sample is performed, at least in part, by a radiating source, a rotating polygon, and a telecentric scan lens.

15. The method of claim 9, wherein the polarizing element is a polarizing beam splitter, and wherein the measuring of specular reflection intensity is performed, at least in part, by an achromatic lens, a bi-cell detector, and the polarizing beam splitter.

16. The method of claim 9, wherein the measuring of specular reflection intensity is performed, at least in part, by an achromatic lens, a bi-cell detector, a polarizing element, and a separation mirror.

* * * * *